United States Patent
Breffa et al.

(10) Patent No.: US 8,008,246 B2
(45) Date of Patent: Aug. 30, 2011

(54) USE OF ISOSORBIDE ETHERS IN DETERGENTS AND CLEANERS

(75) Inventors: Catherine Breffa, Dusseldorf (DE); Burkhard Beckedahl, Dusseldorf (DE); Markus Dierker, Dusseldorf (DE); Ansgar Behler, Dusseldorf (DE); Thorsten Lohl, Schmallenberg (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 12/875,600

(22) Filed: Sep. 3, 2010

(65) Prior Publication Data

US 2011/0059884 A1 Mar. 10, 2011

(30) Foreign Application Priority Data

Sep. 10, 2009 (EP) .................... 09011587

(51) Int. Cl.
C11D 3/20 (2006.01)
C11D 3/22 (2006.01)
C11D 7/26 (2006.01)
C11D 13/10 (2006.01)

(52) U.S. Cl. ........................ 510/505; 510/474

(58) Field of Classification Search .............. 510/474, 510/505
See application file for complete search history.

(56) References Cited

U.S. PATENT DOCUMENTS

2007/0020200 A1   1/2007   Hodosh

FOREIGN PATENT DOCUMENTS

| EP | 186276 | * | 7/1986 |
| EP | 315334 | | 5/1989 |
| EP | 1216685 | | 6/2002 |
| EP | 1621348 | | 2/2006 |

OTHER PUBLICATIONS

Molinier et al, "Isosorbide: A 'Sustainable Diol' Derived From Sorbitol for the Synthesis of New Amphiphiles," Corm V Conference. Meeting Carbohydrates as Organic Raw Materials V—Building a Sustainable Future, Jan. 20, 2009, p. 79, XP002542239.
Chatti et al, "Synthesis of diethers derived from dianhydrohexitols by phase transfer catalysis under microwave," Tetrahedron Letters 41, No. 18 (2000), pp. 3367-3370.

* cited by examiner

*Primary Examiner* — Brian P Mruk
(74) *Attorney, Agent, or Firm* — Diehl Servilla LLC

(57) ABSTRACT

The application pertains to the use of isosorbide ethers according to general formula (I)

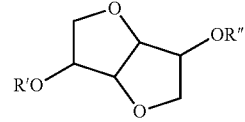

wherein R' and R" independently from each other represent a hydrogen atom or a alkyl- or unsaturated alkenyl moiety for the preparation of detergents and cleaners. Preferably R' and/or R" are linear or branched, saturated or unsaturated alkyl or alkenyl moiety containing 1 to 33 C-Atoms. A second, independent embodiment pertains to the use of these compounds as thickener for aqueous/surfactant compositions.

22 Claims, No Drawings

USE OF ISOSORBIDE ETHERS IN DETERGENTS AND CLEANERS

BACKGROUND OF THE INVENTION

The present application pertains to the use of isosorbide ethers in detergent applications, and the use of the isosorbide ethers as thickener for aqueous compositions.

Isosorbide (or 1,4:3,6-dianhydrosorbitol, see formula below) is the anhydride of sorbitol:

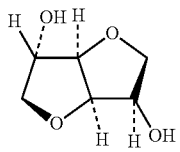

Upon heating sorbitol for example with concentrated sulfuric or hydrochloric acid, two molecules of water are eliminated with the formation of isosorbide. So far, these compounds are also known generally as dianhydrohexitols (including besides isosorbide also the isomers isomannide and isoidide). Besides isosorbide, certain derivatives of isosorbide are well known, inter alia mono- and diesters, and ethers, in particular mono- and dimethylethers of isosorbide. Those ethers are known to have good solvent properties for pharmaceutical and cosmetic compositions. EP 186 276 A2 discloses C1-C4-Alkyldiethers of isosorbide useful in oral hygiene preparations. The document discloses both, symmetrical as well as unsymmetrical ethers. A process for the preparation of such ethers is disclosed in EP 315 334 A2, using dialkylcarbonates and a basic catalyst to etherify the isosorbide. Chatti et al. reported in *Recent Res. Devel. Organic Chem.*, 7 (2003): 13-20 ISBN: 81-7895-093-6 a method to prepare various dialkylethers of isosorbide using microwave irradiation. Isosorbidethers are also known to be suitable in personal care applications, as disclosed in EP 1 216 685 A2.

As isosorbide is derived from natural sources, applicable by double dehydration of starch, it is an interesting basis to obtain new compounds based on renewable resources. In this field, there is a constant search for new derivatives with new properties to suit the needs in some applications areas.

Surface-active formulations such as, for example, manual dishwashing detergents or hair shampoos, liquid detergents or shower gels are more or less concentrated aqueous surfactant preparations that are all expected to have a viscosity which, on the one hand, is low enough to ensure problem-free handling by the user but which, on the other hand, is also high enough to allow economical use. For preparations which are actually marketed in their in-use concentration and which do not have to be diluted by the user at all before use, this means that the water-thin surfactant solutions have to be adjusted to a relatively high viscosity. In many cases, this is done by the addition of electrolyte salts or polymers. However, in critical cases, including for example anionic surfactants containing internal polar groups and, in particular, sugar surfactants of the alkyl glucoside type, this measure is unsuccessful. Thus, the viscosity of alkyl glucoside solutions, for example, can be distinctly reduced by addition of sodium chloride.

SUMMARY OF THE INVENTION

It was found that certain isosorbide derivatives show the capability of thickening aqueous compositions.

A first embodiment of the invention pertains to the use of compounds according to formula (I)

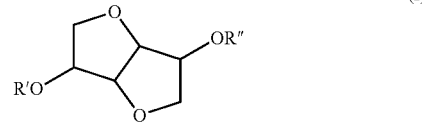

For the preparation of detergents and cleaners, wherein R' and R" independently from each other represent a hydrogen atom or an alkyl- or unsaturated alkenyl moiety. Preferably R' and/or R" represent a linear or branched, saturated or unsaturated alkyl or alkenyl moiety containing 1 to 33 C-Atoms for the preparation of detergents and cleansers (solid, liquid or gel-like ones, or tablets) with the proviso that at least one of the groups R or R' in formula (I) does not represent a hydrogen atom.

The compounds according to formula (I) are ethers of isosorbide. Especially preferred are mono ethers according to formula (I), i.e. R' represents an alkyl- or alkenyl moiety, and R' stands for a hydrogen atom. Further preferred embodiments pertain to those compounds according to formula (I), wherein R' and/or R" is selected from linear saturated alkyl groups, preferably with 6 to 22 and more preferred with 8 to 14 C-atoms. An especially preferred subject matter is isosorbide monoether, wherein R' represents a saturated alkyl chain with 12 C-atoms, whereby R" represents a hydrogen atom. Again, monoethers are in general preferred over diethers.

DESCRIPTION OF THE PREFERRED EMBODIMENTS

The ethers of isosorbide may be obtained by all known methods, preferably by react the isosorbide with halogen alkanes (like alkylchlorides) in the presence of bases. Alternatively, the processes as described in the above mentioned patent applications can be used too.

The isosorbide ethers may then be present in amounts from 0.1 up to 80% by weight, dependent on the particular detergent or cleaner formulation. The isosorbide ethers are particularly useful in home and personal care applications, like all kind of cleaners, as well as in dishwashing compositions.

The isosorbide ethers may be formulated with other surfactants, like anionic, nonionic, amphoteric and/or cationic surfactants, and also different ingredients, known for such compositions, like defoamers, polymers, zeolithes, bleaches, bleach activators, sequestering agents, complexing agents, pH-adjusting agents, dyes, perfumes, enzymes, enzyme stabilization agents, biocides, rheology modifiers, optical brighteners, inorganic salts, hydrotopes, desintegrants, and the like.

Anionic Surfactants

Typical examples of anionic surfactants are soaps, alkylbenzenesulfonates, secondary alkanesulfonates, olefinsulfonates, alkyl ether sulfonates, glycerol ether sulfonates, .alpha.-methyl ester sulfonates, sulfo fatty acids, alkyl and/or alkenyl sulfates, alkyl ether sulfates, glycerol ether sulfates, hydroxy-mixed ether sulfates, monoglyceride (ether) sulfates, fatty acid amide (ether) sulfates, mono- and dialkyl sulfo-succinates mono- and dialkyl sulfosuccinamates, sulfotriglycerides amide soaps, ether carboxylic acids and salts thereof, fatty acid isethionates, fatty acid sarcosinates, fatty acid taurides, N-acyl amino acids such as, for example, acyl lactylates, acyl tartrates, acyl glutamates and acyl aspartates, alkyl oligoglucoside sulfates, protein fatty acid condensates (especially plant products based on wheat), and alkyl (ether) phosphates. Where the anionic surfactants contain polyglycol ether chains, these chains may have a conventional or, preferably, a narrowed homologue distribution.

Nonionic Surfactants

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl-glucamides, protein hydrolysates (especially plant products based on wheat), polyol fatty acid esters, sugar esters, sorbitan esters, polysorbates, and amine oxides. Where the nonionic surfactants contain polyglycol ether chains, these chains may have a conventional or, preferably, a narrowed homologue distribution. Preference is given to using alkyl and/or alkenyl oligoglycosides, further alkoxylated alkanols, hydroxy mixed ethers, fatty acid lower alkyl esters, and amine oxides. Hydroxy mixed ethers constitute also known nonionic surfactants having an asymmetric ether structure and polyalkylene glycol fractions, which are obtained, for example, by subjecting olefin epoxides to a ring opening reaction with fatty alcohol polyglycol ethers. Corresponding products and their use in the field of the cleaning of hard surfaces is subject matter, for example, of the European patent application EP 0639049 and of the international patent application WO 94/22800, and of the documents cited therein.

Preferred nonionic surfactants are alkyl and alkenyl oligoglycosides, which are likewise preferred nonionic surfactants, usually conform to the formula R—O—[G]$_p$ in which R is an alkyl and/or alkenyl radical having 4 to 22 carbon atoms, G is a sugar radical having 5 or 6 carbon atoms and p is a number from 1 to 10. They can be obtained by relevant processes of preparative organic chemistry. The alkyl and/or alkenyl oligoglycosides can be derived from aldoses or ketoses having 5 or 6 carbon atoms, preferably from glucose. The preferred alkyl and/or alkenyl oligoglycosides are thus alkyl and/or alkenyl oligoglucosides. The index number p in the general formula gives the degree of oligomerization (DP), i.e. the distribution of mono- and oligoglycosides, and is a number between 1 and 10. While p in a given compound must always be an integer and can here primarily assume the values p=1 to 6, the value p for a certain alkyl oligoglycoside is an analytically determined calculated parameter which in most cases is a fraction. Preference is given to using alkyl and/or alkenyl oligoglycosides having an average degree of oligomerization p of from 1.1 to 3.0.

Thus, a preferred embodiment of the present invention pertains to the use of the isosorbide ethers according to formula (I) as thickener in aqueous compositions whereby the surfactants in the aqueous compositions are selected from sugar based ones, and preferably from alkyl(oligo)glycosides, as described above.

Amphoteric Surfactants

Amphoteric or Zwitterionic Surfactants Examples of suitable amphoteric or zwitterionic surfactants are alkyl betaines, alkylamido betaines, aminopropionates, aminoglycinates, imidazolinium betaines, and sulfo betaines. Examples of suitable alkyl betaines are the carboxyalkylation products of secondary and especially tertiary amines.

Cationic Surfactants

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry.

The isosorbide ethers according to the present invention are particularly suitable to be included into detergents, preferably laundry detergents, and cleaners, including liquid and solid detergents, and preferably for hard surface cleaners, like kitchen or bathroom cleansers, all purpose cleaners, car wash, or dish washing detergents (for hand washing as well as for automatic dish detergents) and for industrial and institutional cleaning. Examples, which are not limiting the application range, are automatic dishwashing detergents, spray cleaners, bottle cleaning, automotive and locomotive cleaning, high pressure cleaning, tank cleaner and others.

The laundry detergents may comprise the anionic, nonionic and/or amphoteric or zwitterionic or the cationic surfactants in amounts of from 0.5 to 50, preferably from 5 to 25, and in particular from 10 to 20% by weight, based on the laundry detergents. The laundry detergents and cleaning products contain from 0.5 to 25% by weight, preferably from 1 to 15% by weight, in particular from 2 to 10% by weight of surfactants, based on active substance of the formulation.

The laundry detergents and cleaning products may be prepared by spray drying and addition of a liquid or solid surfactant blend to the preparation, but also by spray mixing processes and direct addition to the liquid or solid mixture.

An independent embodiment of the present application pertains to the use of the isosorbide ethers according to formula (I) as thickener for aqueous surfactant compositions, especially for aqueous compositions in the field of detergents, cleaners and cosmetic preparations.

Preferred compounds are the mono ether derivatives. The amount of thickener according to the invention which can be used to thicken aqueous compositions such as detergents, cleaners, and personal care products (which includes shampoos, facial cleaners, liquid hand soaps, and the like) will vary according to the composition of the product to be thickened and is readily determinable by one of ordinary skill in the art. A thickening effective amount will typically range from 0.1% to 5.0% by weight. Thickening means that the viscosity of the aqueous composition will increase after adding the isosorbide ether according to formula (I).

Typically compositions containing the isosorbide derivatives together with a surfactant show viscosities at 21° C. of about 1000 to 5000 mPas.

The thickener compositions according to the invention can be made by mixing it with the other ingredients of the composition using standard mixing equipment.

EXAMPLES

Preparation of the Isosorbide Ethers 12 moles of isosorbide (1753 g) were dissolved in DMSO (900 g) and the mixture was heated to 120° C. Subsequently, 4 mols of NaOH (160 g) were added to the mixture. Once the NaOH addition was completed, 4 mols dodecylchloride were added drop wise to the reaction mixture. Once the reaction was completed, the upper phase was washed with brine 3 times and once with warm water. The raw product is distilled to give 400 g of a light yellow solid. The product is 95% pure according to GC.

Performance Tests of the Isosorbide Derivatives

Thickening Test:

12% Plantapon SF (a sugar based surfactant) and 1% isosorbide-monoether were introduced in a beaker and stirred in the water bath until the monoester was dissolved. The beaker was completed to 100 g with distilled water. The pH value is set to 5.8 through addition of citric acid. After all air bubbles are removed from the solution, and the solution is tempered at 21° C., the viscosity was measured using a viscosimeter 'Brookfield LVT'. For the shorter chains (C12) the isosorbide monoether—surfactant mixes showed viscosities up to 3050 mPas.

Furthermore, 1% Isosorbide lauryl-monoether was added to a standard surfactant system according to the table below. The achieved viscosity of 31.000 to 36.000 mPas at 20° C. shows a very good thickening performance for such a compound.

| Compound | Amount [wt %] |
| --- | --- |
| Sodium Laureth Sulfate | 32.0 |
| Coco-Glucoside | 3.0 |
| Cocamidopropyl Betaine | 3.5 |
| Dyestuff (1% in H$_2$O) | 0.1 |
| Preservative | 0.1 |
| NaCl | 2.5 |
| Water | 57.8 |
| Thickening Agent | 1.0 |

The invention claimed is:

1. Method of preparing a detergent or cleanser comprising the step of adding to said detergent or cleanser, an isosorbide ether according to general formula (I)

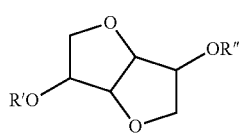

(I)

wherein R' and R" independently from each other represent a hydrogen atom or a C6-C33 alkyl- or a C6-C33 unsaturated alkenyl moiety, with the proviso that at least one group R' or R" is not a hydrogen atom.

2. The method of claim 1, wherein R' and/or R"-represent a linear or branched, saturated or unsaturated alkyl or unsaturated alkenyl moiety.

3. The method of claim 2, wherein R' and/or R" is selected from linear saturated alkyl groups of 6 to 22 carbon atoms.

4. The method of claim 3, wherein the linear saturated alkyl groups have 8 to 14 carbon atoms.

5. The method of claim 4, wherein R' represents a saturated alkyl chain with 12 carbon atoms and R" represents a hydrogen atom.

6. The method of claim 1, wherein the isosorbide ether is combined with at least one of anionic, nonionic, amphoteric, cationic or zwitterionic surfactants, defoamer, zeolith, bleach, bleach activator, sequestering agent, complexing agent, pH-adjusting agent, dye, perfume, enzyme, enzyme stabilization agent, biocides, rheology modifier, optical brightener, inorganic salt, hydrotope and desintegrant.

7. The method of claim 1, wherein the isosorbide ether is added in an amount from 0.1 up to 80% by weight of the detergent or cleanser.

8. The method of claim 5, wherein the isosorbide ether is combined with sodium lauryl sulfate surfactant.

9. A method of thickening an aqueous surfactant composition comprising the step of adding to said surfactant composition, an isosorbide ether according to general formula (I)

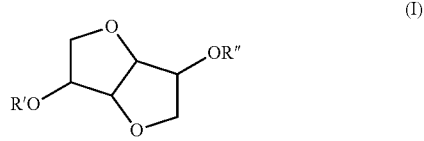

(I)

wherein R' and R" independently from each other represent a hydrogen atom or a C6-C33 alkyl- or a C6-C33 unsaturated alkenyl moiety, with the proviso that at least one group R' or R" is not a hydrogen atom.

10. The method according to claim 9, wherein the surfactant composition comprises a surfactant selected from sugar based surfactants.

11. The method according to claim 9, wherein the isosorbide ether is added in an amount of from 0.1 to 5.0% by weight of the resulting composition.

12. The method according to claim 9 wherein the isosorbide ether is added to the surfactant to provide viscosity at 21° C. of about 1000 to 5000 mPas.

13. The method according to claim 10, wherein said surfactant is selected from alkyl(oliog)glycosides.

14. An aqueous surfactant composition comprising surfactant and, as thickening agent for said surfactant, an isosorbide ether according to general formula (I)

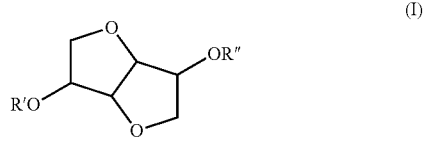

(I)

wherein R' and R" independently from each other represent a hydrogen atom or a C6-C33 alkyl- or a C6-C33 unsaturated alkenyl moiety with the proviso that at least one group R' or R" is not a hydrogen atom, in an amount effective to thicken the surfactant composition.

15. The composition according to claim 14, wherein the surfactant composition comprises a surfactant selected from sugar based surfactants.

16. The composition of claim 14, wherein the isosorbide ether is present in an amount from 0.1% to 5.0% by weight of the composition.

17. The composition of claim 14, wherein the isosorbide ether is present in an amount to provide viscosity at 21° C. of about 1000 to 5000 mPas.

18. The composition of claim 14, wherein R' and/or R"-represent a linear or branched, saturated or unsaturated alkyl or unsaturated alkenyl moiety.

19. The composition of claim 18, wherein R' and/or R" is selected from linear saturated alkyl groups of 6 to 22 carbon atoms.

20. The composition of claim 19, wherein the linear saturated alkyl groups have 8 to 14 carbon atoms.

21. The composition of claim 20, wherein R' represents a saturated alkyl chain with 12 carbon atoms and R" represents a hydrogen atom.

22. The composition according to claim 15, wherein said surfactant is selected from alkyl(oliog)glycosides.

* * * * *